United States Patent [19]
Nihei et al.

[11] Patent Number: 5,442,155
[45] Date of Patent: Aug. 15, 1995

[54] WELDING POSITION DETECTOR WITH COOLING AND CLEANING MEANS

[75] Inventors: Ryo Nihei, Fujiyoshida; Yasuo Sasaki; Takahiro Hase, both of Yamanashi, all of Japan

[73] Assignee: Fanuc Ltd., Yamanashi, Japan

[21] Appl. No.: 302,415

[22] Filed: Sep. 8, 1994

[30] Foreign Application Priority Data

Sep. 8, 1993 [JP] Japan .................................. 5-223470

[51] Int. Cl.6 ............................................. B23K 9/095
[52] U.S. Cl. ............................ 219/130.01; 219/124.34; 359/509
[58] Field of Search ...................... 219/130.01, 130.21, 219/124.34, 147; 359/509

[56] References Cited

U.S. PATENT DOCUMENTS

| | | | |
|---|---|---|---|
| 4,491,715 | 1/1985 | Voronin et al. ........................ | 219/74 |
| 4,555,613 | 11/1985 | Shulman ........................... | 219/124.34 |
| 4,652,133 | 3/1987 | Antoszewski et al. .............. | 356/376 |
| 4,658,113 | 4/1987 | Vingerling ........................... | 219/147 |
| 4,784,491 | 11/1988 | Penney et al. ....................... | 356/376 |
| 4,794,223 | 12/1988 | Barkman et al. ................. | 219/124.34 |
| 4,859,829 | 8/1989 | Dufour ............................. | 219/124.34 |
| 4,896,247 | 1/1990 | Cozer ................................. | 361/385 |
| 5,264,678 | 11/1993 | Powell et al. .................. | 219/130.01 |

*Primary Examiner*—Clifford C. Shaw
*Attorney, Agent, or Firm*—Nikaido, Marmelstein, Murray & Oram

[57] ABSTRACT

A cooling and cleaning unit incorporated in a welding position detector having a gas introducing conduit for introducing a single flow of a cooling gas under pressure into a hermetically sealed chamber of a casing for encasing therein a sensor unit of the welding position detector in the form of a convectional flow of cooling gas circulating around the sensor unit and removing heat from the sensor unit, a check valve unit having a gas inlet and a gas outlet and permitting the cooling gas under pressure to be discharged from the hermetically sealed chamber toward an outer face of a protective window of the welding position detector in the form of cleaning gas under pressure to thereby clean the outer face of the protective window while forming a gas curtain extending over the outer face of the protective window so as to prevent welding fumes and sputter from attaching to and depositing onto the outer face of the protective window of the welding position detector.

4 Claims, 2 Drawing Sheets

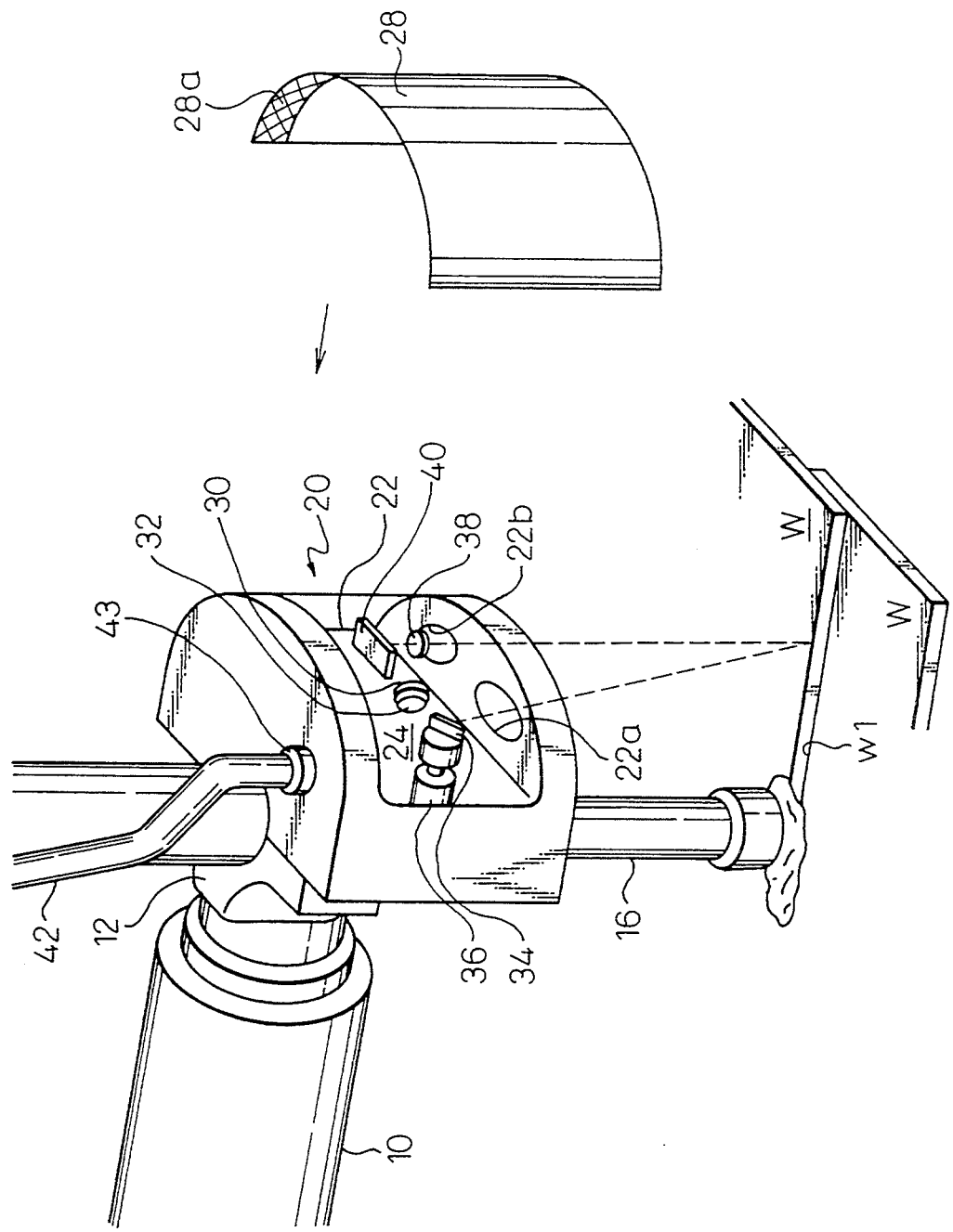

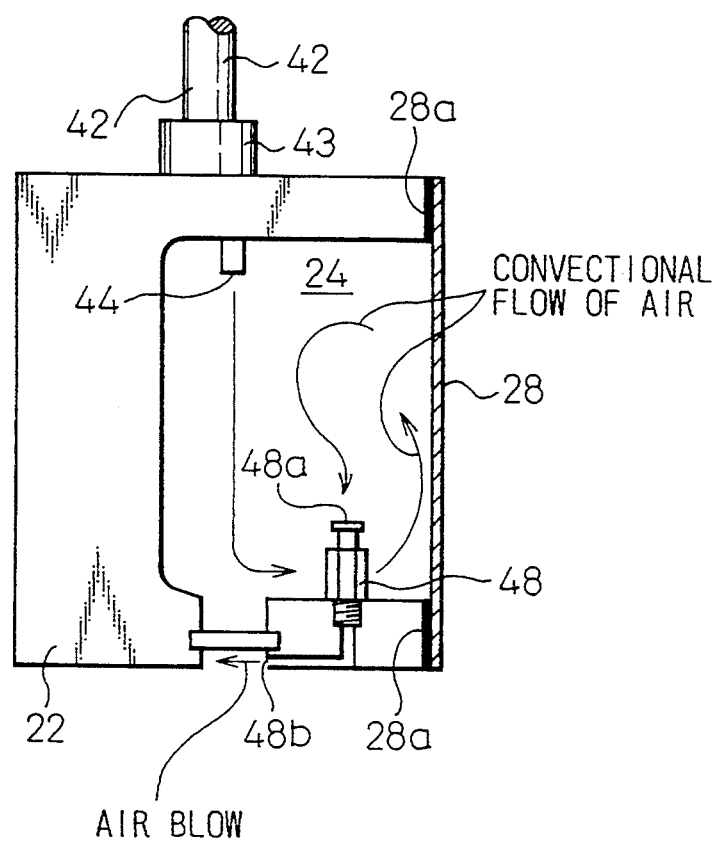

WELDING POSITION DETECTOR WITH COOLING AND CLEANING MEANS

BACKGROUND OF THE INVENTION

1. Field of the Invention

The present invention relates generally to an apparatus for protecting a welding position detector which is attached to an extreme end of a multi-articulated type industrial robot, i.e., an arc-welding robot, to detect an arc-welding position on a workpiece welded by an arc-welding torch attached to the extreme end of the arc-welding robot. More particularly, it relates to a cooling and cleaning apparatus for preventing a sensor unit sealably encased in the housing arc-welding position of the welding position detector from being damaged by heat generated at welded positions to the workpiece and from contamination by fumes and welding-sputter during welding.

2. Description of the Related Art

Arc-welding robots are frequently used in the field of manufacturing and assembling automobiles and of assembling structural elements of buildings, and arc-welding robots are constructed as a multi-articulated type industrial robot having a robot wrist on which an arc-welding torch and an arc sensor are mounted. The arc sensor of an arc-welding robot detects welding positions along a desired welding line on a workpiece, and sends the detected data to a robot controller. Thus, the robot controller controls the motion of the moving elements of the arc-welding robot according to the detected data to thereby transfer the arc-welding torch to an objective position suitable for applying arc-welding to the detected welding positions of the workpiece along the desired welding line. Nevertheless, the arc sensor has recently been modified into a different type arc-welding position sensor referred to as an optical arc-welding position detector which can be mounted on the conventional arc-welding robot in the same manner as the arc sensor.

The optical arc-welding position detector mounted on the arc-welding robot is provided with a light-emitting element in the form of a semi-conductor laser arranged so as to emit a laser beam illuminating the surface of the welded workpiece, and a light-receiving element in the form of a charge-coupled device (CCD) arranged so as to receive the laser beam when it is reflected by the surface of the workpiece to thereby obtain data of the configuration of the workpiece surface on the basis of the received laser beam. This type of arc-welding position detector is also provided with a casing for containing therein the above-mentioned sensor unit including the semiconductor laser, an objective lens element, an assembly of a galvanometric device and a mirror for providing the emitting laser with scanning action against the surface of a welded workpiece, the light-emitting element in the form of the CCD, and a light-receiving lens element. The casing of the arc-welding position detector is covered with a window made of a transparent resin material and the like, in order to protect all of the above-mentioned sensor unit from contamination by the fumes and welding-sputter during the arc-welding operational.

When the optical welding-position detector is used with the arc-welding robot for, for example, welding either ceiling portions in the interior of each vehicle body in a car assembling station or high corner portions of metallic frameworks of a building at a building site, a problem occurs that the above-mentioned protective window of the arc-welding position detector is unavoidably contaminated by attachment or deposition of welding-sputter resulting in making it impossible to emit a detecting laser beam and to receive the laser beam reflected from the welded positions. Namely, when the arc-welding robot must be used in such a position and posture that the welding torch and the protective window of the arc-welding position detector are positioned so as to be directed upward, the welding fume and the welding-sputter fall down and are attached to or deposited onto the face of the window of the arc-welding position detector during the welding operation of the robot. Thus, the arc-welding position detector using the laser beam as a position detecting medium cannot achieve accurate detection of the welding positions on the surface of the workpiece.

In order to solve the above-mentioned problem, Japanese Unexamined Patent Publication (Kokai) No. 6-91586 filed by the same assignee as the present U.S. Patent application has already disclosed a proposal for cleaning the window of the arc-welding position detector by supplying pressurized gas, preferably pressurized air, to the face of the window. The pressurized air cleans the external face of the window of the arc-welding position detector and forms an external air-curtain covering and protecting the external face of the window.

Nevertheless, the sensor unit, i.e., the semiconductor laser, the CCD type light-receiving element, and the other electronic and optical elements encased in the outer casing of the welding-position detector are not durable against heat. Therefore, an arrangement of an appropriate cooling means for cooling the above-mentioned sensor unit encased in the outer casing of the welding-position detector is indispensable for enhancing the thermal durability of the detector to thereby increase the operation life and accuracy in the detection of the welding position.

In order to effectively cool the encased electronic and optical elements including the semiconductor laser and the CCD type light-sensing element, it is necessary to supply a flow of cooling gas, particularly a cooling air, into the interior of the casing of the welding-position detector so as to directly remove heat from the electronic and optical elements. However, if both the formation of the above-mentioned external curtain and the supply of the cooling air are individually implemented by using independent flows of gas, two separate gas supply systems and various flow control valves are needed, and accordingly, it is impossible to simplify the peripheral arrangement of the optical welding-position detector and to reduce the size of the optical welding-position detector. As a result, the optical welding-position detector must suffer from an inconvenience that the detector is unable to detect welding positions located in a narrow region of a welded object such as an interior of a vehicle body.

SUMMARY OF THE INVENTION

An object of the present invention is to provide a compact cooling and cleaning unit for applying not only a cooling effect to an internal sensor unit of an optical welding-position detector but also a cleaning effect to the external face of a window of the detector without being contaminated by welding fumes and welding sputter.

Taking the above object into consideration, the present invention provides a cooling and cleaning unit adapted for being incorporated in an optical welding position detector of an arc-welding apparatus which unit uses a single line of pressurized gas flow, preferably a flow of pressurized clean air. The cooling and cleaning unit can introduce the flow of the pressurized clean air into a hermetically sealed chamber defined by a casing of the welding position detector to thereby remove heat from a sensor unit including a semiconductor laser for emitting a laser beam for detection, an optical elements such as an objective lens and a light-receiving lens, a CCD type laser beam sensing element, and other electronic and optical elements encased in the casing. The cooling and cleaning unit further allows the pressurized clean air to be spouted from the chamber of the casing via a check valve toward an outer face of a light transmitting window of the casing of the welding position detector in the form of a jetting flow of the pressurized air to thereby form an air curtain cleaning and covering the outer face of the window. Thus, the outer face of the window of the welding position detector is constantly kept clean so that emission of the laser beam from the semiconductor laser and entrance of the laser beam reflected from a surface of a welded object into the chamber of the welding position detector are not prevented by the contamination of the window.

In accordance with the present invention, there is provided a cooling and cleaning unit adapted for being incorporated in a welding position detector having a casing unit encasing a sensor unit emitting a laser beam for detection purposes to thereby illuminate a welded area of a welded object, via a protective window of the casing, and receiving the laser beam reflected by the welded area of the welded object, via the protective window to thereby detect the welded area of the welded object, the cooling and cleaning unit removing heat from the sensor unit by using a single flow of cooling gas and protecting an outer face of the protective window of the detector from contamination. The cooling and cleaning unit for the welding position detector comprises a single gas introducing unit for introducing a single flow of cooling gas under pressure into a hermetically sealed chamber defined in the, casing of the welding position detector, a gas discharging unit for permitting the cooling gas to be discharged into the hermetically sealed chamber in the form of a convectional flow of cooling gas circulating around the sensor unit to thereby remove heat from the sensor unit, and a check valve unit for permitting the cooling gas to be delivered from the hermetically sealed chamber of the welding position detector toward outside the casing, the check valve unit being arranged in the casing and having a gas inlet opening into the hermetically sealed chamber for introducing the cooling gas and a gas outlet opening toward an outer face of the protective window of the welding position detector for spouting the cooling gas in the form of a laminar flow of pressurized cleaning gas streaming on the outer face of the window to thereby form a gas curtain protecting the outer face of the window from contamination.

Preferably, the cooling gas introduced into the chamber of the casing of the welding position detector comprises a single flow of clean air under an appropriate pressure, filtered by an air filter means arranged in the gas introducing means.

BRIEF DESCRIPTION OF THE DRAWINGS

The above and other objects, features, and advantages of the present invention will be made by the ensuing description of a preferred embodiment thereof with reference to the accompanying drawings wherein:

FIG. 1 is a perspective view of a welding position detector having a part thereof dismantled and equipped with a cooling and cleaning unit according to an embodiment of the present invention, the welding position detector cooperating with a multi-articulated industrial arc-welding robot provided with an arc-welding torch; and FIG. 2 is a schematic view of the welding position detector of FIG. 1, schematically illustrating the operation principle of the cooling and cleaning unit.

DESCRIPTION OF THE PREFERRED EMBODIMENT

Referring to FIG. 1, a multi-articulated type industrial robot is provided with a wrist element 10 attached to an extreme end of an arm system of the robot. The wrist element 10 has an end thereof to which a bracket member 12 is attached for fixedly connecting an arc-welding torch 16 to the wrist element 10. The arc-welding torch 16 is used for connecting, e.g., two plate-like workpieces W by welding. The portion of the workpieces W to be welded is referred to as a desired welded portion W1 of the workpiece or similar welded object. The industrial robot having the above-mentioned arm system and the wrist element 10 controls movement of the arc-welding torch 16 so that an accurate welding is applied to the desired welded portion W1 of the welded object W under the control of a robot controller (not shown in the drawings).

The welding torch 16 is provided with a welding position detector 20 which operates so as to detect a desired welded portion W1 of the welded object W in advance, and delivers information of the detected position in the form of a detected feedback signal toward the robot controller. Thus, the robot controller controls the motion of the arc-welding robot to thereby control the arc-welding torch 16. Thus, the arc-welding torch 16 welds the welded object W at the desired welded portion W1 thereof. This welding operation of the arc-welding torch 16 on the basis of the detection of the desired welded portion W1 made in advance by the welding position detector 20 is continuously performed until the welding of the welded object W is completed.

The welding position detector 20 is provided with a hollow casing 22 made of a metallic or resin material and having an internal chamber 24 for encasing therein a sensor unit including various electronic and optical elements such as a semiconductor type laser 30 emitting a laser beam for detection purpose, an objective lens element 32 advancing the laser beam emitted by the laser 30 toward a desired direction, a scanning mirror 34 rotatively driven by a galvanometric device 36 so as to advance the laser beam coming from the objective lens element 32 toward the surface of the welded object W via an emitting window 22a of the casing 22 while applying scanning motion to the laser beam in a direction perpendicular to the advancing direction of the laser beam, a light-receiving lens element 38 receiving, via a receiving window 22b of the casing 22, the laser beam reflected by the surface of the welded object W when it illuminates the surface, and a CCD-type sensing element 40 for detecting the welded portion W1 of the welded object W. The CCD-type sensing element 40 operates so as to obtain two-dimensional coordinate data of the illuminated portion of the welded object W from the rotating angle of the scanning mirror 34 and the coordinate data formed in the CCD-type sensing element per se, and to detect the welded portion W1 of the welded object W.

The above-mentioned sensor unit of the welding position detector 20 is assembled into the internal chamber 24 of the casing 22 via a front opening 22c when a cover 28 is removed from the casing 22. The cover 28 is attached to the front side of the casing 22 in the direction of an arrow shown in FIG. 1 and hermetically closes the opening 22c by using a hermetic-seal element 28a provided at a margin of the cover 28. Thus, the internal chamber 24 of the casing 22 can be hermetically sealed against the exterior of the welding position detector 20.

The sensing system and operation of the welding position detector 20 is equivalent to the conventional optical welding position detector.

Nevertheless, in accordance with the present invention, the welding position detector 20 is further provided with a novel cooling and cleaning unit described hereinbelow.

The casing 22 of the welding position detector 20 has a top face to which a gas introducing conduit 42 is sealably fixed by an appropriate pipe coupling or nipple 43 so that a cooling gas under an appropriate pressure, typically a pressurized air, is introduced from a suitable gas supply source (not shown) into the casing 22 of the welding position detector 20. The cooling gas under pressure is then discharged into the internal chamber 24 via a gas discharge port 44 arranged in an upper part of an inner wall of the casing 22. Thus, the discharged cooling gas, e.g., a pressurized cooling air, forms a convectional flow of pressurized cooling air circulating around the sensor unit encased in the internal chamber 24 of the casing 22. Therefore, the pressurized cooling air removes heat from the sensor unit, and accordingly, the semiconductor laser 30, the galvanometric device 36, and the other electronic and optical elements within the internal chamber 24 can be protected against heat, and constantly maintain ordinary operation thereof. Further, the thermal distortion of the optical elements such as lens and mirror elements 32, 34 and 38 can be prevented. Thus, an accurate detection of the welded portion W1 of the welded object W can be ensured for a long operation life of the welding position detector 20.

Referring now to FIG. 2, the cooling principle of the cooling and cleaning unit using the cooling gas under appropriate pressure is schematically illustrated.

In FIG. 2, the afore-mentioned gas discharge port 44 is provided so as to open into the internal chamber 24 of the casing 22 to thereby discharge the cooling gas under pressure, e.g., the pressurized cooling air, into the internal chamber 24 in the form of a jetting stream of the cooling gas. The discharged cooling air circulates in the internal chamber 24 forming a convectional flow of the cooling air passing by the sensor unit within the chamber 24, and therefore, even if heat generated from the welded portion W1 of the welded object W is transmitted to the casing 22, the sensor unit encased in the casing 22 can be protected against heat by the heat removing action of the circulated cooling air.

The cooling and cleaning unit according to the present invention is further provided with a check valve unit 48 provided in the internal chamber 24 of the casing 22 at a position opposite to the gas discharge port 44.

The check valve unit 48 permits the cooling gas under pressure to flow therethrough so as to come out of the chamber 24 toward the exterior of the casing 22 after cooling action. On the other hand, the check valve unit 48 prevents reversal of flow of the cooling gas under pressure, and entrance of an external air and other gas from coming into the internal chamber 24 of the casing 22 therethrough. The check valve unit 48 is provided with a gas inlet 48a located in the internal chamber 24 of the casing 22 so as to permit the cooling gas under pressure to flow into the valve unit 48 from the internal chamber 24, and a gas outlet 48b provided outside the casing 22 and located adjacent to the light-emitting window 22a and the light-receiving window 22b arranged in a protective window of the casing 22.

Therefore, the cooling gas under pressure, i.e., the pressurized cooling air after cooling action is permitted to flow out of the internal chamber 24 of the casing 22 through the discharge outlet 48b of the check valve 48 toward outer faces of both windows 22a and 22b in the form of the jetting stream of the gas under pressure referred to as "AIR BLOW" in FIG. 2, and cleans the outer faces of both windows 22a and 22b of the casing 22 of the welding position detector 20. The jetting stream of the gas under pressure further forms a gas curtain extending along the outer faces of the windows 22a and 22b the protective window of the casing 22. Thus, the gas curtain can prevent the welding fumes and the welding sputter which are generated at the welded portion W1 of the welded object W from attaching to and depositing onto the outer faces of the above-mentioned windows 22a and 22b. Namely, the gas curtain formed by the jetting stream of the gas under pressure prevents these outer faces of the windows 22a and 22b from being contaminated.

From the foregoing description of the preferred embodiment of the present invention, it will be understood that a single flow of cooling gas under appropriate pressure, preferably a flow of pressurized air, is introduced by the gas introducing conduit 42 having therein an appropriate filtering element, at first cools the sensor unit in the hermetically sealed chamber 24 of the casing of the welding position detector 20, and subsequently cleans the outer faces of the light-emitting and light-receiving windows 22a and 22b of the casing 22 during streaming of the internal chamber 24 while preventing attachment or deposition of the welding fumes and sputter onto the outer faces of the windows 22a and 22b.

Accordingly, it will be understood that effective use of a single flow of gas under pressure not only for cooling purposes but also for cleaning purposes can be achieved by the cooling and cleaning unit of the present invention. As a result, when the cooling and cleaning unit of the present invention is incorporated in the welding position detector of an arc-welding apparatus, e.g., an industrial arc-welding robot, and when the arc-welding apparatus is used in a posture standing upward so as to perform welding operation at a higher position, the welding position detector can exhibit a constant and stable position detecting function without being adversely affected by welding heat, fumes, and sputter.

Moreover, the cooling and cleaning unit of a welding position detector according to the present invention can be compact in size owing to the effective use of a single flow line of cooling gas, and therefore, the welding position detector can be used for detecting a welded position in a narrow space of a welded object such as an internal space of a car body and a corner portion of a steel framework of a building.

Furthermore, since the cooling and cleaning unit of the welding position detector according to the present invention is provided with a check valve unit capable of preventing reverse flow of gas from the exterior of the detector into the hermetically sealed internal chamber of the detector, the sensor unit encased in the chamber is not subjected to contamination during the welding operation, and accordingly, a reduction in the detecting performance of the welding position detector can be prevented.

It should be understood that various modifications may occur to persons skilled in the art without departing from the scope and spirit of the invention claimed in the accompanying claims.

We claim:

1. A cooling and cleaning means adapted for being incorporated in a welding position detector having a casing means encasing a sensor unit emitting a laser beam for detection to thereby illuminate a welded area of a welded object, via a protective window means of said casing means, and receiving the laser beam reflected by the welded area of the welded object, via said protective window means to thereby detect the welded area of the welded object, said cooling and cleaning means removing heat from said sensor unit by using a single flow of cooling gas under pressure and protecting an outer face of said protective window means of said welding position detector from contamination, said cooling and cleaning means for said welding position detector comprising:

a single gas introducing means for introducing the single flow of pressurized cooling gas into a hermetically sealed chamber defined in said casing means of said welding position detector;

a gas discharging means for permitting the cooling gas under pressure to be discharged into said hermetically sealed chamber in the form of a convectional flow of gas circulating around said sensor unit to thereby remove heat from said sensor unit; and, a check valve means for permitting the cooling gas under pressure to be delivered from said hermetically sealed chamber of the welding position detector toward the outside of the casing, said check valve means being arranged in said casing means and having a gas inlet opening into said hermetically sealed chamber for introducing the cooling gas under pressure and a gas outlet opening toward an outer face of said protective window of said welding position detector for spouting the cooling gas under pressure in the form of a laminar flow of pressurized cleaning gas streaming on said outer face of said protective window means to thereby form a gas curtain protecting said outer face of said window means from contamination.

2. A cooling and cleaning means according to claim 1, wherein said gas discharging means is provided with a gas discharge port arranged at a portion of an inner wall of said casing means so as to open into said hermetically sealed chamber of said casing means, and wherein said check valve means is arranged in said hermetically sealed chamber at a position opposing to said gas discharge port, said gas inlet of said check valve means permitting the cooling gas to be introduced into said check valve means, and said gas outlet of said check valve means permitting the introduced cooling gas to be discharged toward said outer face of said protective window means.

3. A cooling and cleaning means according to claim 2, wherein said gas outlet of said check valve means is arranged adjacent to said outer face of said protective window means.

4. A cooling and cleaning means according to claim 1, wherein the single flow of cooling gas under pressure comprises a single flow of pressurized air.

* * * * *